United States Patent
Miyazawa

(10) Patent No.: US 9,398,887 B2
(45) Date of Patent: Jul. 26, 2016

(54) RADIATION IMAGING CONTROL APPARATUS, METHOD OF CONTROLLING RADIATION IMAGING CONTROL APPARATUS, MEDICAL IMAGING APPARATUS, MEDICAL IMAGE DISPLAY METHOD, AND STORAGE MEDIUM

(71) Applicant: CANON KABUSHIKI KAISHA, Tokyo (JP)

(72) Inventor: Nobu Miyazawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 290 days.

(21) Appl. No.: 14/061,894

(22) Filed: Oct. 24, 2013

(65) Prior Publication Data

US 2014/0119514 A1    May 1, 2014

(30) Foreign Application Priority Data

Oct. 31, 2012   (JP) ................................. 2012-241105

(51) Int. Cl.
*A61B 5/00* (2006.01)
*A61B 6/00* (2006.01)
*G06F 19/00* (2011.01)

(52) U.S. Cl.
CPC .............. *A61B 6/463* (2013.01); *G06F 19/321* (2013.01); *G06F 19/3406* (2013.01); *A61B 6/465* (2013.01); *A61B 6/50* (2013.01); *A61B 6/545* (2013.01); *A61B 6/563* (2013.01)

(58) Field of Classification Search
CPC .......... A61B 6/542; A61B 6/467; A61B 6/54; A61B 6/465; A61B 6/463
See application file for complete search history.

(56) References Cited

U.S. PATENT DOCUMENTS

| 2002/0082484 | A1* | 6/2002 | Baba ...................... A61B 6/463 600/300 |
| 2003/0142119 | A1* | 7/2003 | Akagi .................. A61B 6/4216 345/698 |
| 2005/0100136 | A1* | 5/2005 | Kawatsu ................ A61B 6/463 378/207 |
| 2005/0154767 | A1* | 7/2005 | Sako ........................ A61B 6/00 |
| 2008/0095418 | A1  | 4/2008 | Moriya ......................... 382/128 |
| 2010/0246925 | A1* | 9/2010 | Nagatsuka ............... A61B 5/08 382/132 |
| 2011/0311026 | A1* | 12/2011 | Lalena ................. A61B 6/4405 378/98.5 |
| 2012/0183188 | A1* | 7/2012 | Moriya ................. G06F 19/321 382/128 |
| 2013/0077746 | A1* | 3/2013 | Tsuji ...................... A61B 6/463 378/62 |
| 2013/0088512 | A1* | 4/2013 | Suzuki .................. G06Q 10/06 345/629 |

FOREIGN PATENT DOCUMENTS

| JP | A 2008-102665 | 5/2008 |
| JP | A 2010-022653 | 2/2010 |
| JP | A 2011-125355 | 6/2011 |
| JP | A 2012-035124 | 2/2012 |

* cited by examiner

*Primary Examiner* — Hoon Song
(74) *Attorney, Agent, or Firm* — Fitzpatrick, Cella, Harper & Scinto

(57) ABSTRACT

A medical imaging apparatus which captures a medical image based on imaging technique information includes a display control unit which displays thumbnails of medical images captured based on imaging technique information in a first area on a display window, displays a thumbnail of a different-inspection image retrieved based on the imaging technique information in a second area, and displays, in a third area, a medical image corresponding to a selected thumbnail of the thumbnails displayed in the first area.

21 Claims, 9 Drawing Sheets

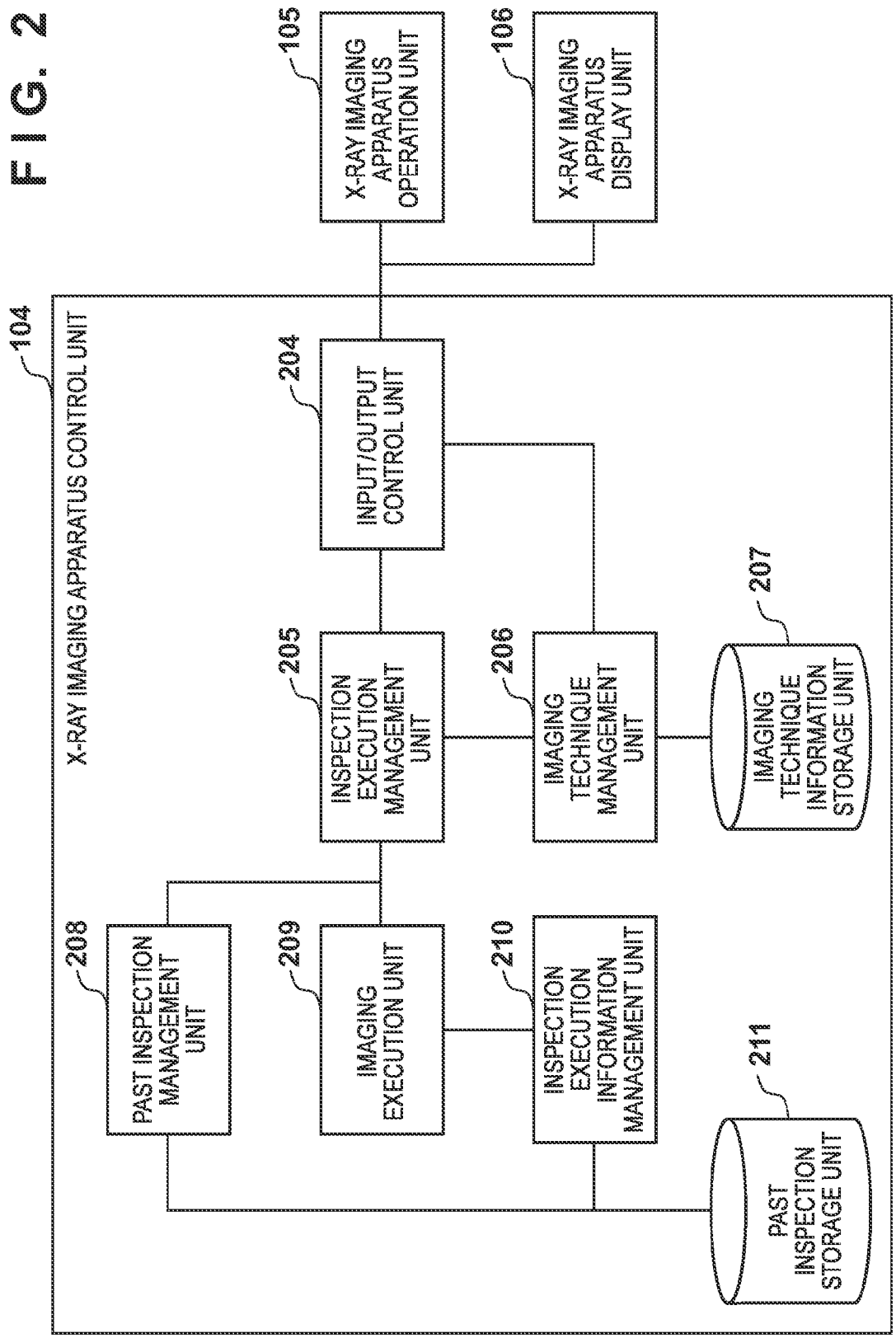

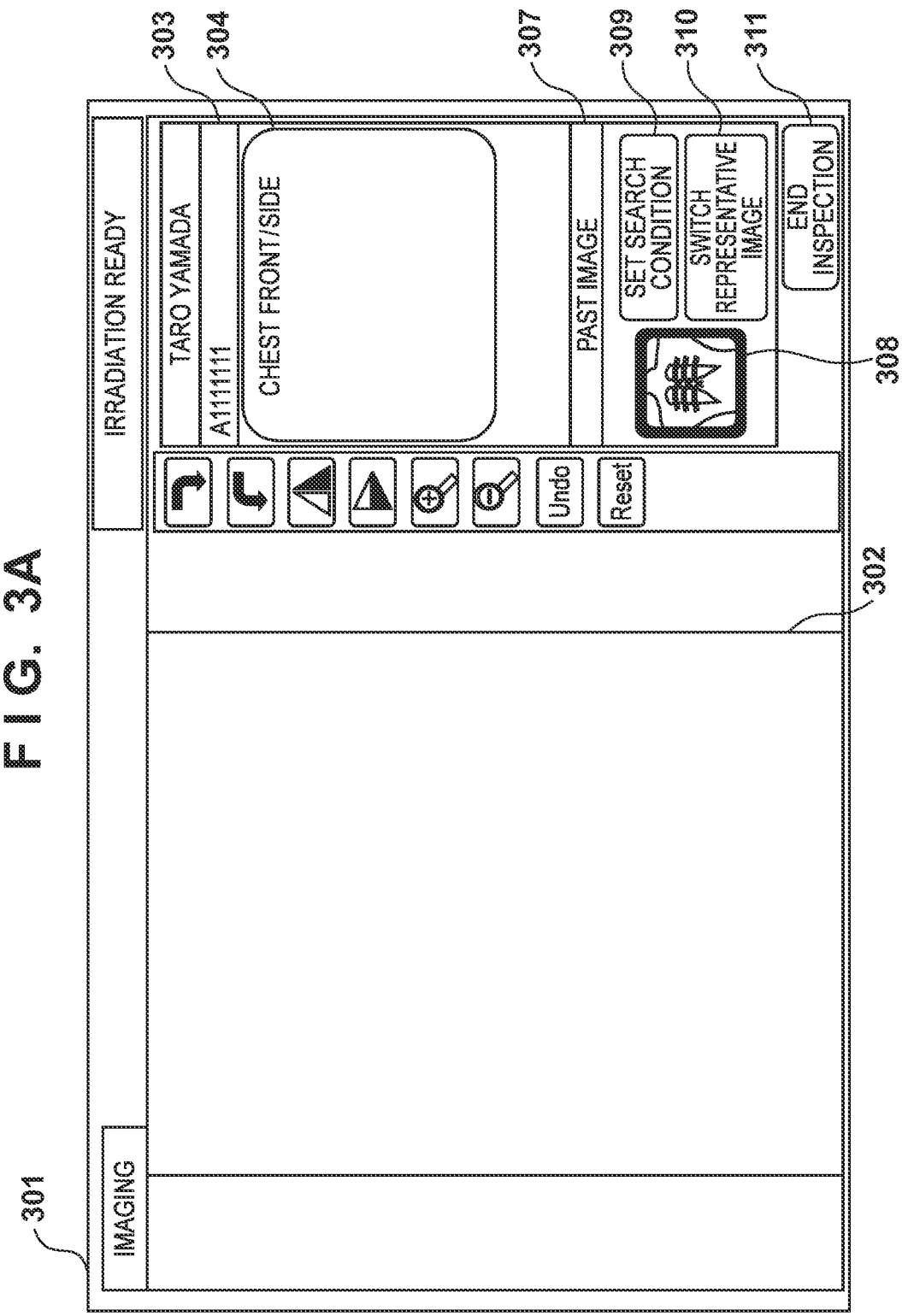

FIG. 4

401 PAST IMAGE SEARCH CONDITION SETTINGS

402 ● AND SEARCH  ○ OR SEARCH

403 ■ PATIENT INFORMATION
■ PATIENT NAME  ■ PATIENT ID  ☐ BIRTH DATE  ☐ AGE  ☐ SEX  · · ·

404 ■ IMAGING TECHNIQUE INFORMATION
■ IMAGING TECHNIQUE NAME  ■ IMAGING PORTION  ☐ IMAGING DIRECTION  · · ·
☐ CLIPPING SETTING  ☐ PRINT OUTPUT SETTING

405 ■ IRRADIATION CONDITION INFORMATION
■ TUBE VOLTAGE [kV]  ■ TUBE CURRENT [mA]  ☐ mAs VALUE [mAs]  · · ·
☐ IRRADIATION TIME [ms]  ☐ BINNING

406 Cancel   407 OK

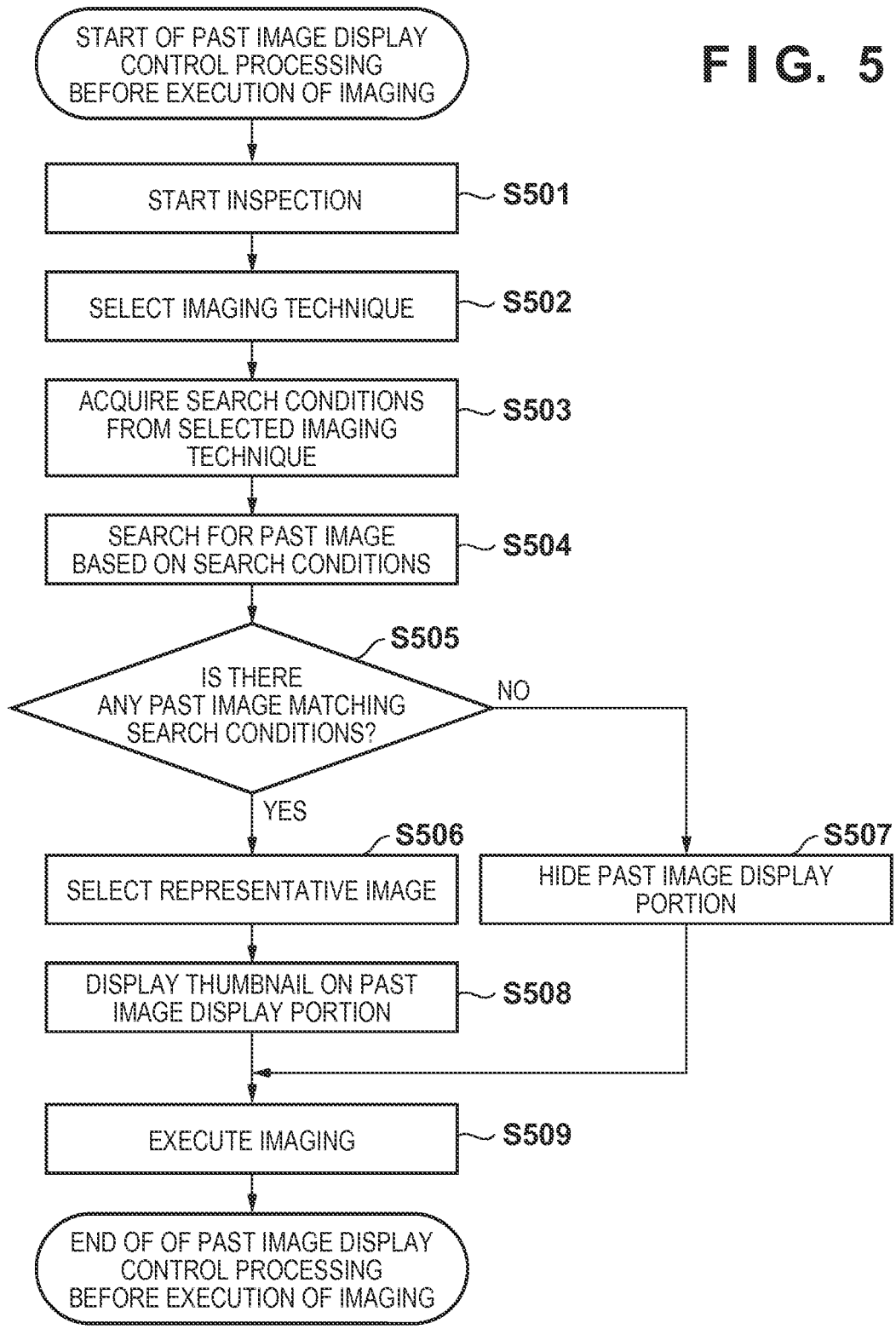

FIG. 7

| INSPECTION ID | INSPECTION DATE | INSPECTION DESCRIPTION | A1111111 CHEST FRONT/SIDE |
|---|---|---|---|
| A1111111 | 2011/01/01 17:18:20 | abcdefg | |
| B1234567 | 2012/01/07 12:28:51 | ABCDEFG | |
| ... | ... | ... | RETURN |

PATIENT NAME: TARO YAMADA  PATIENT ID: 1234567

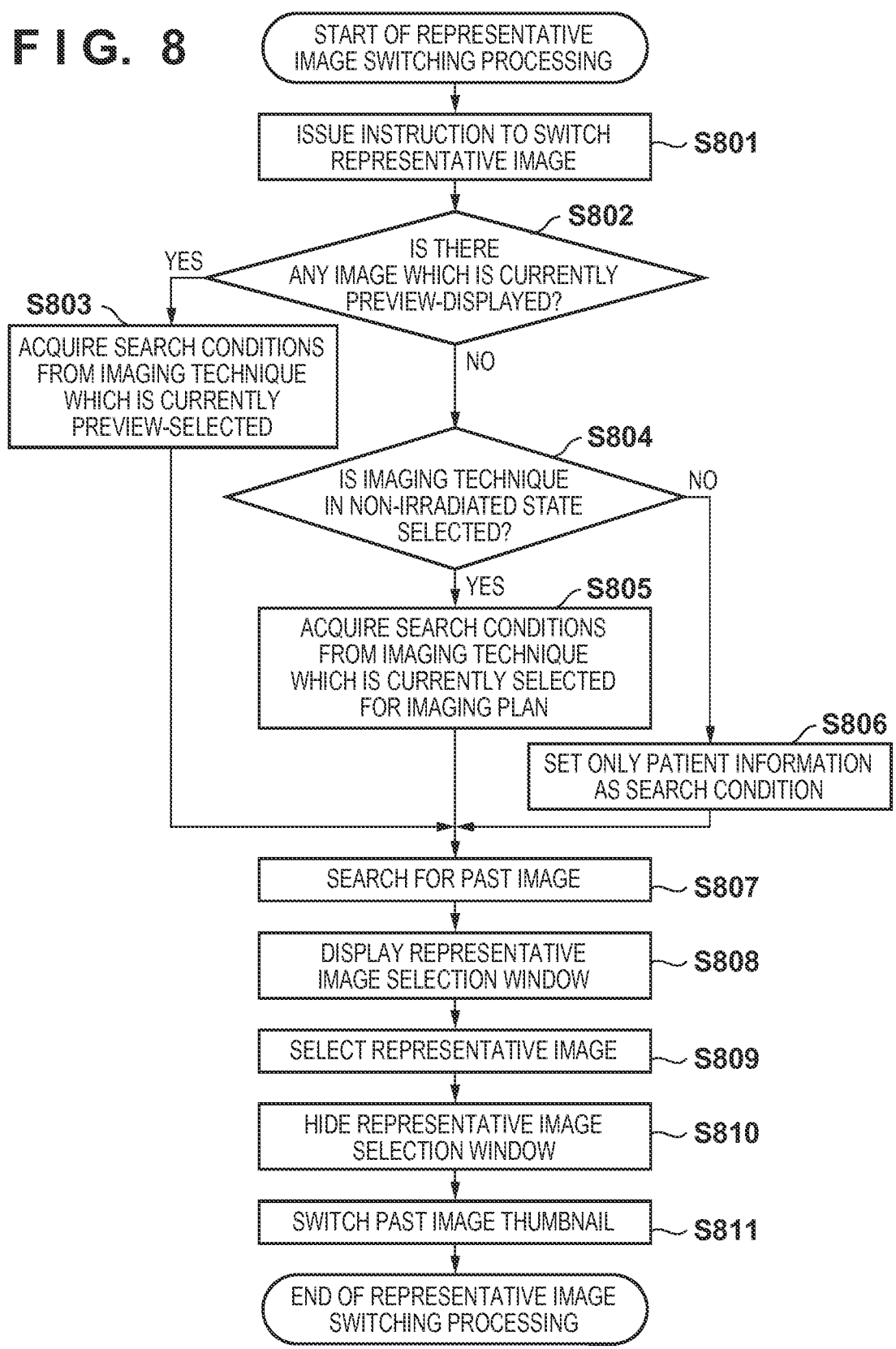

RADIATION IMAGING CONTROL APPARATUS, METHOD OF CONTROLLING RADIATION IMAGING CONTROL APPARATUS, MEDICAL IMAGING APPARATUS, MEDICAL IMAGE DISPLAY METHOD, AND STORAGE MEDIUM

BACKGROUND OF THE INVENTION

1. Field of the Invention

The present invention relates to a radiation imaging control apparatus, a method of controlling a radiation imaging control apparatus, a medical imaging apparatus, a medical image display method, and a storage medium.

2. Description of the Related Art

Conventionally, medical imaging apparatuses have been widely used as apparatuses for capturing "medical images" used when doctors and the like check and diagnose the medical conditions of patients. Various types of medical imaging apparatuses are available, including an X-ray imaging apparatus and X-ray CT apparatus using X-rays, an MRI (Magnetic Resonance Imaging) apparatus, a nuclear medicine imaging apparatus typified by a PET or SPECT, and an ultrasonic imaging apparatus. There are also available various types of medical images captured by a medical imaging apparatus, ranging from morphological images to images captured by imaging functional values such as a blood flow to the brain.

For this reason, a doctor or the like determines a medical image suitable for diagnosis for each patient and uses a medical imaging apparatus capable of capturing the medical image to acquire a desired medical image.

When checking and diagnosing the medical condition of a patient by using an acquired medical image, a doctor or the like performs comparative interpretation by making the apparatus display, for example, a medical image of the same patient captured in the past and the currently captured medical image on the same display window side by side. Alternatively, the doctor performs diagnosis while comparing the currently captured medical image with a case image suitable for the main purpose of the diagnosis using the medical image upon displaying the images side by side.

For this reason, the medical imaging apparatus is preferably configured to perform preview display of a medical image captured in a past inspection (to be referred to as a different-inspection image hereinafter) in the currently executed inspection.

This is because it is possible to perform comparative interpretation faster than an interpretation system such as Viewer if it is possible to perform preview display of an image captured in the current inspection as a medical image immediately after imaging (to be referred to as a captured image hereinafter) and a different-inspection image arranged side by side.

When performing follow-up observation of the same patient, it is necessary to match imaging states at the time of the current imaging operation such as the posture and imaging direction of the patient and the aperture of a collimator with those at the time of the previous imaging operation. Displaying a different-inspection image is therefore effective in grasping the imaging state at the time of the previous imaging before the current imaging operation.

When, however, a medical imaging apparatus is configured to display captured images and different-inspection images on the same display window side by side, display for a patient with many different-inspection images may suffer a shortage of display area on a display window. In addition, if many different-inspection images are displayed on a display window, it is difficult to discriminate captured images from the different-inspection images, and it is also difficult to identify a desired different-inspection image (a different-inspection image suitable for comparison).

In contrast to this, Japanese Patent Laid-Open No. 2008-102665 has proposed an arrangement configured to search for a similar case image based on the characteristics of a captured image in the first imaging operation and search for a different-inspection image of the same imaging portion in the second and subsequent imaging operations. Japanese Patent Laid-Open No. 2010-022653 has proposed an arrangement configured to search for different-inspection images of the same patient and display them on a display window different from the display window of a captured image.

SUMMARY OF THE INVENTION

According to one aspect of the present invention, there is provided a radiation imaging control apparatus which uses a radiation detector for obtaining a radiation image, the apparatus comprising: a display control unit configured to display an imaging window for controlling radiation imaging on a display unit, wherein the imaging window includes display areas for displaying at least one imaging condition included in one inspection, a captured image obtained based on the imaging condition, and a radiation image of an inspection different from the inspection, and in accordance with selection of an imaging condition which has not been used for imaging among the displayed imaging conditions, the display control unit controls the radiation detector and displays the radiation image of the different inspection based on the imaging condition.

According to the present invention, it is possible to improve convenience to the operator of a medical imaging apparatus which can display different-inspection images.

Further features of the present invention will become apparent from the following description of exemplary embodiments (with reference to the attached drawings).

BRIEF DESCRIPTION OF THE DRAWINGS

FIG. 2 is a block diagram showing the functional arrangement of an X-ray imaging control unit 104;

FIG. 3A is a view showing an example of a display window displayed on the X-ray imaging apparatus 101 before the execution of imaging;

FIG. 4 is a view showing a display window to be displayed when a search condition setting button 309 is pressed;

FIG. 5 is a flowchart showing a procedure for different-inspection image display control processing before the execution of imaging;

FIG. 7 is a view showing an example of a display window to be displayed when a representative image switching button 310 is pressed; and FIG. 8 is a flowchart showing a procedure for representative image switching processing.

DESCRIPTION OF THE EMBODIMENTS

Each embodiment will be described in detail below with reference to the accompanying drawings. Although each embodiment to be described below will exemplify an X-ray imaging apparatus as a medical imaging apparatus, the medical imaging apparatus to which each embodiment is applied is not limited to the X-ray imaging apparatus, and each embodiment may be applied to other types of medical imaging apparatuses.

First Embodiment

<1. Overall Arrangement of X-Ray Imaging System>

Figure 1:
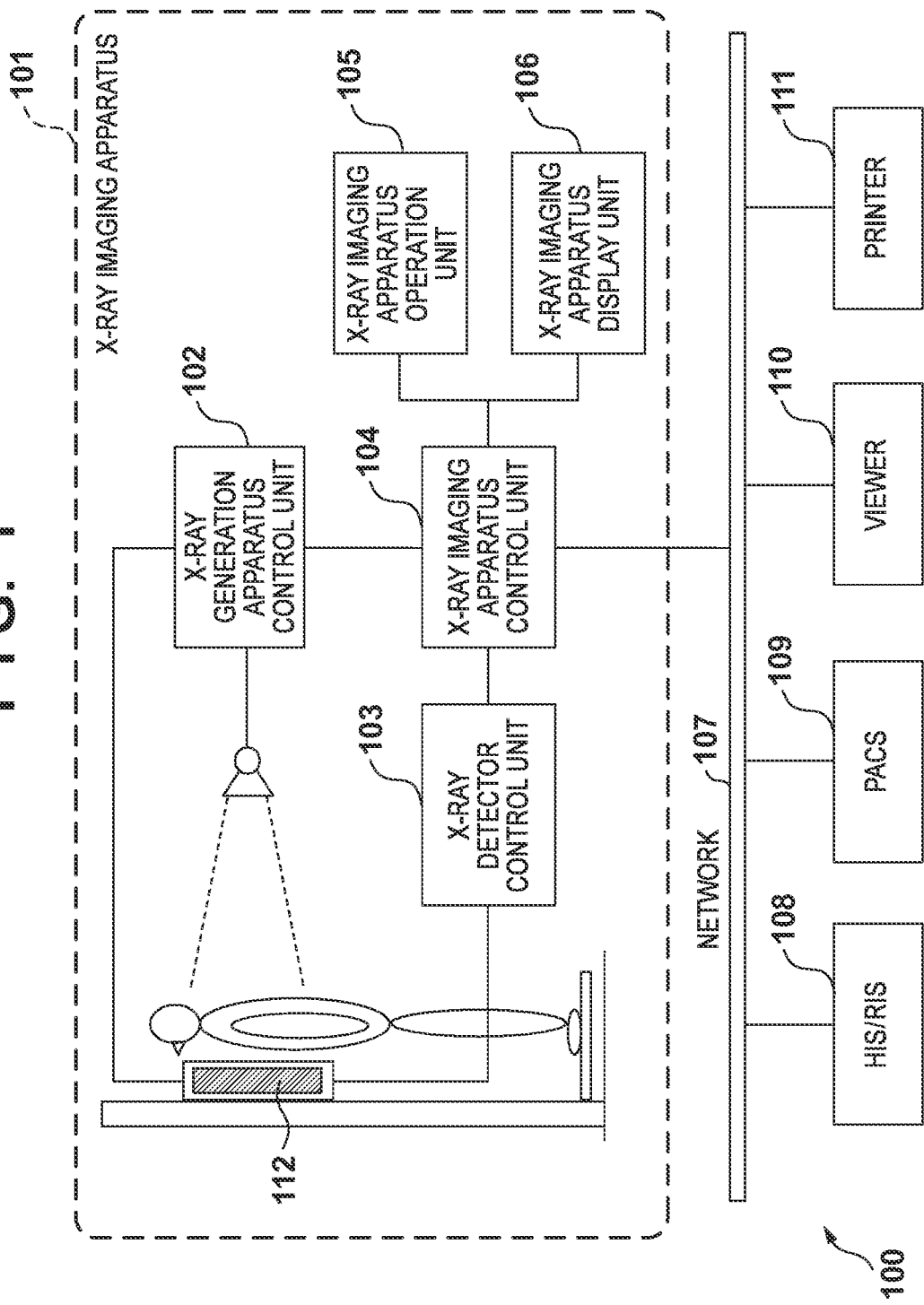
FIG. 1 is a block diagram showing the overall arrangement of an X-ray imaging system 100 including an X-ray imaging apparatus 101 according to an embodiment.

The overall arrangement of an X-ray imaging system will be described first. FIG. 1 is a block diagram showing the overall arrangement of an X-ray imaging system 100 including an X-ray imaging apparatus 101 according to an embodiment.

As shown in FIG. 1, the X-ray imaging system 100 includes the X-ray imaging apparatus 101, a HIS/RIS 108, a PACS 109, a Viewer 110, and a printer 111. They are communicatively connected to each other via a network 107.

The HIS/RIS 108 is a management apparatus which manages patient information in a radiological department. The PACS 109 is a server apparatus for storing images captured in the current inspection (captured images). Note that the captured images include actual images captured in the current inspection, and display images to be reduced in size, as needed, and displayed in an image display portion 302. The Viewer 110 is a display apparatus which displays the image captured by the X-ray imaging apparatus 101 and is used for image inspection processing, detailed postprocessing, diagnostic processing, and the like. The printer 111 is an output apparatus which prints out a captured image.

The X-ray imaging apparatus 101 includes an X-ray generation apparatus control unit 102 which is connected to an X-ray generation apparatus which generates X-rays, and an X-ray detector control unit 103 connected to an X-ray detector 112. The X-ray detector 112, for example, includes a scintillator for converting an X-ray beam into a visible light beam, a sensor including a plurality of pixels for detecting the visible light beam and obtaining electric signals. The X-ray detector 112 also includes a drive circuit for setting the sensor in a first state for accumulating the electric signals in the pixels and setting the sensor in a state for outputting the accumulated electric signals from the pixels. And the X-ray detector 112 includes amplifier for amplify the electric signals and includes analog-digital convertor for converting the amplified electric signals into digital signals. It also includes an X-ray imaging apparatus control unit 104, an X-ray imaging apparatus operation unit 105, and an X-ray imaging apparatus display unit 106.

The X-ray generation apparatus control unit 102 notifies the X-ray generation apparatus of an X-ray irradiation request and irradiation conditions such as a tube voltage and a tube current. The X-ray detector control unit 103 notifies the X-ray detector 112 of imaging conditions such as a read area, and receives captured images for the apparatus. The X-ray imaging apparatus control unit 104 performs overall control including control on inspection processing, management of "inspection information" at the time of inspection processing, communication with an external device, and storage/readout control of captured images. Note that the X-ray imaging apparatus control unit 104 can be configured as a single control apparatus. The control apparatus includes, for example, a CPU, a ROM, a RAM, a communication circuit, a hard disk drive (HDD), and programs stored in the HDD. The programs include those for executing processes shown in FIGS. 5, 6, and 8. The HDD stores the data and programs of windows shown in FIGS. 3A, 3B, 4, and 7.

In this case, "inspection information" includes "patient information" including information for specifying a patient such as a patient name and a patient ID, and "inspection content identification information" including all information for specifying an inspection such as an inspection ID and an inspection date. Assume that "inspection information" also includes "imaging technique information" including all information for specifying an imaging technique such as an imaging portion, and "image information" including a captured image, an image ID, and an image attribute.

The X-ray imaging apparatus operation unit 105 is an input device including a keyboard and a mouse, and functions as an input interface which receives the contents of operation by the operator. Each type of information input via the X-ray imaging apparatus operation unit 105 is transmitted to the X-ray imaging apparatus control unit 104.

The X-ray imaging apparatus display unit 106 is a display apparatus such as a separate display or a monitor incorporated in the X-ray imaging apparatus 101, and functions as an output interface which displays a captured image or the like. Note that the X-ray imaging apparatus display unit 106 may be implemented by a multi-touch monitor combined with the X-ray imaging apparatus operation unit 105.

<2. Functional Arrangement of X-Ray Imaging Apparatus Control Unit>

The functional arrangement of the X-ray imaging apparatus control unit 104 will be described next. FIG. 2 is a view for explaining the functional arrangement of the X-ray imaging apparatus control unit 104. Referring to FIG. 2, an input/output control unit 204 performs communication between the X-ray imaging apparatus operation unit 105 and the X-ray imaging apparatus display unit 106. Note that various types of information input via the X-ray imaging apparatus operation unit 105 are transmitted as various types of notifications to the input/output control unit 204. Display control is performed on the X-ray imaging apparatus display unit 106 in accordance with the display update notification transmitted from the input/output control unit 204.

Upon receiving each type of notification from the X-ray imaging apparatus operation unit 105, the input/output control unit 204 transmits the received notification content to an inspection execution management unit 205 and/or an imaging technique management unit 206. In addition, the input/output control unit 204 transmits a display update notification to the X-ray imaging apparatus display unit 106 based on a request from the inspection execution management unit 205 and/or the imaging technique management unit 206.

The inspection execution management unit 205 controls the overall processing executed by the X-ray imaging apparatus 101 during the execution of an inspection. Note that the contents of processing executed during the execution of an inspection include inspection start/end processing, captured image/different-inspection image thumbnail display control processing, and captured image/different-inspection image preview display control processing.

The imaging technique management unit 206 performs registration/update/deletion/search and the like of imaging technique information selected during the execution of an inspection. More specifically, when the input/output control unit 204 transmits imaging technique information search notification, the imaging technique management unit 206 acquires retrieved imaging technique information from an imaging technique information storage unit 207 and transmits it to the input/output control unit 204. Upon receiving an imaging technique information registration notification from the input/output control unit 204, the imaging technique management unit 206 transmits a registration notification to the imaging technique information storage unit 207. In addition, upon receiving an inspection start notification from the inspection execution management unit 205, the imaging technique management unit 206 acquires imaging technique information from the imaging technique information storage unit 207 and transmits it to the inspection execution management unit 205.

In this case, "imaging technique information" includes items ranging from information for specifying an imaging technique such as an imaging portion and an imaging direction to irradiation conditions, image processing parameters, storage transfer settings, and print output settings. In other words, this information includes all the items which can be set for each imaging technique in the process from inspection processing to postprocessing and image output processing.

The imaging technique information storage unit 207 is formed from a database and performs search, registration, and the like of imaging technique information in accordance with a search notification, registration notification, and the like of imaging technique information from the imaging technique management unit 206.

A past inspection management unit 208 manages different-inspection images captured in inspections executed in the past. More specifically, upon receiving a different-inspection image search notification from the inspection execution management unit 205, the past inspection management unit 208 transmits the different-inspection image search notification to a past inspection storage unit 211 so as to search for a different-inspection image based on preset search conditions and the imaging technique information added to the different-inspection image search notification. Upon receiving a search result from the past inspection storage unit 211, the past inspection management unit 208 transmits a search end notification added with the received search result to the inspection execution management unit 205.

An imaging execution unit 209 manages overall processing associated with X-ray imaging. More specifically, upon receiving a status notification, X-ray irradiation start notification, or X-ray irradiation end notification from the X-ray detector 112 or X-ray generation apparatus, the imaging execution unit 209 transmits each notification to the inspection execution management unit 205. In addition, upon receiving actual irradiation conditions (execution irradiation conditions) after receiving an X-ray irradiation end notification, the imaging execution unit 209 transmits the execution irradiation conditions to an inspection execution information management unit 210.

The inspection execution information management unit 210 stores and updates inspection information. More specifically, upon receiving an inspection end notification from the inspection execution management unit 205, the inspection execution information management unit 210 transmits a storage notification for the storage of inspection information including a captured image to the past inspection storage unit 211.

The past inspection storage unit 211 is formed from a database, and stores executed inspection information (inspection information including the currently captured image and reflecting execution irradiation conditions and the like) notified from the inspection execution information management unit 210. The past inspection storage unit 211 also searches for a different-inspection image in accordance with the different-inspection image search notification transmitted from the past inspection management unit 208 or the inspection execution information management unit 210.

<3. Description of Display Windows Displayed on X-Ray Imaging Apparatus Display Unit 106>

The display windows displayed on the X-ray imaging apparatus display unit 106 will be described next with reference to FIGS. 3A, 3B, and 4.

<3.1 Description of Display Window Displayed During Execution of Inspection>

The display window displayed during the execution of an inspection will be described first. FIGS. 3A and 3B each show an example of a display window 301 displayed on the X-ray imaging apparatus display unit 106 during the execution of an inspection. FIG. 3A shows an example of a display window before the execution of imaging. FIG. 3B shows an example of a display window after the execution of imaging.

Referring to FIG. 3A, reference numeral 302 denotes an image display portion on which a captured image or the like is displayed; and 303, a currently executed inspection information display portion on which patient information such as a patient name and inspection content identification information such as an inspection ID are displayed. The currently executed inspection information display portion 303 includes an imaging technique display portion 304 (first display portion) on which an imaging technique name is displayed.

Reference numeral 307 denotes a different-inspection image display portion (second display portion) including a search condition setting button 309 which is pressed to set search conditions for searching for a different-inspection image. The different-inspection image display portion 307 also includes a representative image switching button 310 which is pressed to switch the representative image selected from the retrieved different-inspection image group. In addition, the different-inspection image display portion 307 includes a different-inspection image thumbnail display area 308 in which a thumbnail of the representative image selected from the retrieved different-inspection image group is displayed (that is, the different-inspection image thumbnail display area 308 functions as a second display control unit). Note that the display window to be displayed when the operator presses the search condition setting button 309 and the representative image switching button 310 will be described in detail later.

Reference numeral 311 denotes an inspection end button 311 which is pressed to issue an inspection end instruction.

Figure 3B:
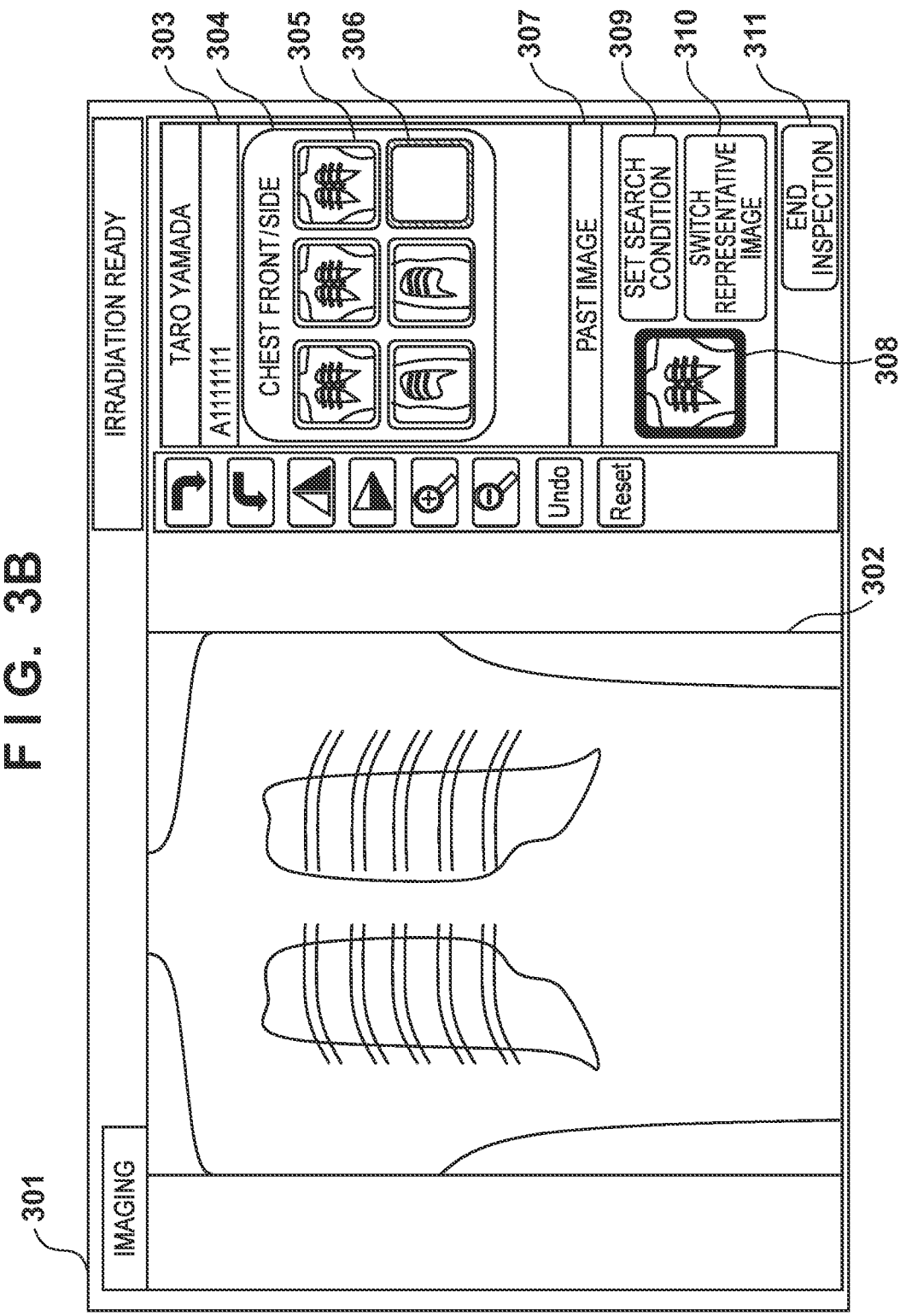
FIG. 3B is a view showing an example of a display window displayed on the X-ray imaging apparatus 101 after the execution of imaging.

FIG. 3B shows an example of a display window displayed after the execution of imaging. As shown FIG. 3B, the apparatus displays captured image thumbnail display areas 305 of the imaging technique display portion 304 and then displays thumbnails of the images captured based on the corresponding imaging technique information (that is, the imaging technique display portion 304 functions as a first display control unit). Note that a captured image thumbnail display area 306 is an area in which a thumbnail of the image to be captured is displayed.

The apparatus automatically displays the currently captured image on the image display portion 302. Note that when the operator preview-selects any of the thumbnails displayed on the imaging technique display portion 304, the apparatus preview-displays the captured image corresponding to the selected thumbnail (that is, the image display portion 302 functions as a third display control unit). When the operator preview-selects the thumbnail displayed in the different-inspection image thumbnail display area 308 on the different-inspection image display portion 307, the apparatus preview-displays a different-inspection image corresponding to the selected thumbnail.

<3.2 Description of Display Window Displayed when Search Condition Setting Instruction Portion is Pressed>

A display window (different-inspection image search condition setting window) to be displayed when the operator presses the search condition setting button 309 on the display window 301 will be described next. FIG. 4 shows an example of a display window 401 to be displayed when the operator presses the search condition setting button 309.

As shown in FIG. 4, the display window 401 includes a search method selection portion 402, a patient information setting portion 403, an imaging technique information setting portion 404, an irradiation condition information setting unit 405, a cancel instruction portion 406, and a change confirmation instruction portion 407.

The search method selection portion 402 is an area for designating either AND search or OR search if there are a plurality of items selected as search conditions in each of the patient information setting portion 403, the imaging technique information setting portion 404, and the irradiation condition information setting unit 405.

The patient information setting portion 403 is an area for individually designating whether to use patient information as a search condition and whether to use each item (patient name, patient ID, . . . ) included in patient information as a search condition.

The imaging technique information setting portion 404 is an area for individually designating whether to use imaging technique information as a search condition and whether to use each item (imaging technique name, imaging portion, . . . ) included in imaging technique information as a search condition.

The irradiation condition information setting unit 405 is an area for independently designating whether to use information concerning irradiation conditions as a search condition and whether to use each item (tube voltage, tube current, . . . ) included in irradiation condition information as a search condition.

The cancel instruction portion 406 is a button for inputting an instruction to discard a changed content. The change confirmation instruction portion 407 is a button for inputting an instruction to store a changed content.

<4. Procedure for Display Control Processing in X-Ray Imaging Apparatus>

A procedure for different-inspection image display control processing before and after imaging by the X-ray imaging apparatus 101 will be described next. As described above, when using the X-ray imaging apparatus 101, displaying a different-inspection image before imaging is effective in matching an imaging state at the previous imaging operation with that at the current imaging operation when, for example, performing follow-up observation of the same patient. In addition, displaying a different-inspection image after imaging is effective in performing comparative interpretation with a captured image.

For this reason, when the operator selects imaging technique information before imaging, the X-ray imaging apparatus 101 automatically searches for a different-inspection image based on the selected imaging technique information and displays a thumbnail of the different-inspection image on the different-inspection image display portion 307.

When imaging is complete and the captured image is displayed on the image display portion 302, the apparatus automatically searches for a different-inspection image based on the information of the imaging technique actually used at the time of imaging for the captured image, and displays a thumbnail of the different-inspection image on the different-inspection image display portion 307.

When the operator selects any of the thumbnails displayed on the imaging technique display portion 304 and the captured image displayed on the image display portion 302 is changed, the apparatus automatically re-searches for a different-inspection image based on the imaging technique information of the changed captured image. The apparatus is also configured to update the thumbnail display on the different-inspection image display portion 307 based on the re-retrieved different-inspection images.

As described above, the X-ray imaging apparatus 101 is configured to sequentially search for a different-inspection image corresponding to imaging technique information and automatically update the different-inspection image displayed on the different-inspection image display portion 307. This makes it possible to display, on the different-inspection image display portion 307, a different-inspection image effective in comparing with the captured image displayed on the image display portion 302. Display control processing in the X-ray imaging apparatus 101 will be described in detail below separately concerning different-inspection image display control processing before the execution of imaging and different-inspection image display control processing after the execution of imaging.

<4.1 Procedure for Different-Inspection Image Display Control Processing Before Execution of Imaging>

A procedure for different-inspection image display control processing before the execution of imaging in the X-ray imaging apparatus 101 will be described first by using FIG. 5 with reference to FIGS. 2 and 3A. FIG. 5 is a flowchart showing a procedure for different-inspection image display control processing before the execution of imaging in the X-ray imaging apparatus 101.

In step S501, when the operator inputs an inspection start instruction, the apparatus receives this instruction and transmits an inspection start notification to the input/output control unit 204.

Upon receiving the inspection start notification, the input/output control unit 204 transmits the inspection start notification to the inspection execution management unit 205. Upon receiving the inspection start notification, the inspection execution management unit 205 acquires imaging technique information of the imaging technique to be executed from the imaging technique information storage unit 207 via the imaging technique management unit 206. The inspection execution management unit 205 also controls the X-ray imaging apparatus display unit 106 via the input/output control unit 204 to display the display window 301 (FIG. 3A).

In step S502, the operator selects an imaging technique based on the display window 301 (FIG. 3A) displayed on the X-ray imaging apparatus display unit 106, and the X-ray imaging apparatus operation unit 105 receives this selection.

Note that the operator may manually select an imaging technique by, for example, pressing the imaging technique display portion 304, or the apparatus may automatically select an imaging technique in a non-imaged state. When the operator has manually selected an imaging technique, the X-ray imaging apparatus operation unit 105 transmits an imaging technique selection notification to the inspection execution management unit 205 via the input/output control unit 204. When automatically selecting an imaging technique, the inspection execution management unit 205 automatically selects an imaging technique in a non-imaged state.

Upon receiving an imaging technique selection notification, the inspection execution management unit 205 transmits an irradiation permission request notification to the imaging execution unit 209, together with the selected imaging technique information. Upon receiving the irradiation permission request notification, the imaging execution unit 209 transmits the irradiation permission request notification to the X-ray generation apparatus and the X-ray detector 112 to shift them to an irradiation enable state.

The X-ray detector control unit 103 transmits a control signal to the X-ray detector 112 in accordance with the selection of imaging conditions. This control signal is a signal for instructing operation corresponding to the selected imaging conditions. If, for example, an abdominal region is set as an imaging target in the imaging conditions, the X-ray detector control unit 103 transmits a control signal including an instruction to perform operation by setting an accumulation time to three times a normal one. Alternatively, for example, if the imaging conditions are limited to an irradiation region, the X-ray detector control unit 103 transmits a control signal including an instruction not to operate the A/D convertor, amplifier, pixels other than the irradiation region. In this way, the X-ray detector control unit 103 controls the X-ray detector 112 in accordance with the imaging conditions.

In step S503, the apparatus acquires search conditions for searching for a different-inspection image based on the imaging technique information selected in step S502. More specifically, the inspection execution management unit 205 transmits a different-inspection image search request notification to the past inspection management unit 208. The past inspection management unit 208 transmits the different-inspection image search condition request notification to the past inspection storage unit 211, together with patient information/inspection content identification information and the transmitted imaging technique information. Upon receiving the different-inspection image search condition request notification, the past inspection storage unit 211 acquires items to be used from the search conditions stored in advance (the search conditions set via the display window 301). The operator then decides the specific values of the respective items of search conditions based on the transmitted patient information/inspection content identification information and the imaging technique information, and transmits the decided values to the past inspection management unit 208.

In step S504, the apparatus searches for a different-inspection image based on the decided search conditions. More specifically, the past inspection management unit 208 transmits a different-inspection image search notification to the past inspection storage unit 211, together with the decided search conditions. Upon receiving the different-inspection image search notification, the past inspection storage unit 211 searches for past inspection information based on the decided search conditions and transmits a different-inspection image group as a search result to the past inspection management unit 208.

In step S505, the past inspection management unit 208 checks whether a different-inspection image group has been transmitted as a search result. If the past inspection management unit 208 determines that a different-inspection image group matching the decided search conditions has been retrieved and transmitted as a search result, the process advances to step S506.

In step S506, the apparatus selects a representative image from the search result. More specifically, the past inspection management unit 208 selects, as a representative image, the latest different-inspection image (the different-inspection image captured at the latest imaging time) from the different-inspection image group as the search result. This is because different-inspection images to be comparatively interpreted are mainly those captured at the immediately preceding imaging times. However, the method of deciding representative images is not limited to this, and representative images may be decided by other methods. In addition, the number of representative images to be selected is preferably one, but may be plural depending on the size of the different-inspection image display portion 307. Upon deciding a representative image, the past inspection management unit 208 transmits image information including the different-inspection image as the representative image to the inspection execution management unit 205.

In step S508, the apparatus displays a thumbnail of the representative image on the different-inspection image display portion 307. More specifically, upon receiving the image information including the different-inspection image as the representative image, the inspection execution management unit 205 displays a thumbnail of the representative image on the different-inspection image display portion 307 of the X-ray imaging apparatus display unit 106 via the input/output control unit 204.

With this operation, the operator can preview-display the representative image by pressing the thumbnail of the representative image on the display window 301. Note that since the different-inspection image display portion 307 displays only the representative image selected from a different-inspection image group as a search result, the problem that the different-inspection image display portion 307 is wasted is solved.

If the inspection execution management unit 205 determines in step S505 that there is no different-inspection image group matching the search conditions, the apparatus hides the different-inspection image display portion 307 in step S507. This makes it possible to prevent the different-inspection image display portion 307 from being wasted in spite of the fact that there is no different-inspection image to be comparatively interpreted as in the case of a patient at the initial visit.

In step S509, the imaging execution unit 209 executes imaging. With this operation, the apparatus terminates the different-inspection image display control processing before imaging.

As described above, the X-ray imaging apparatus 101 according to this embodiment is configured to access the past inspection storage unit 211 storing past inspection information before the execution of imaging based on selected imaging technique information to acquire search conditions for searching for a different-inspection image. This makes it possible to search for a desired different-inspection image corresponding to the current imaging technique and display the different-inspection image before imaging. In addition, when displaying a different-inspection image, the apparatus displays only a representative image of a retrieved different-inspection image group on the different-inspection image display portion 307. This can facilitate discriminating a captured image from a different-inspection image and prevent the different-inspection image display portion 307 from being wasted.

In the display control processing shown in FIG. 5, the apparatus executes imaging in step S509. However, this embodiment is not limited to this and may execute imaging at any timing after the selection of an imaging technique in step S302.

<4.2 Procedure for Different-Inspection Image Display Control Processing after Execution of Imaging>

Figure 6:
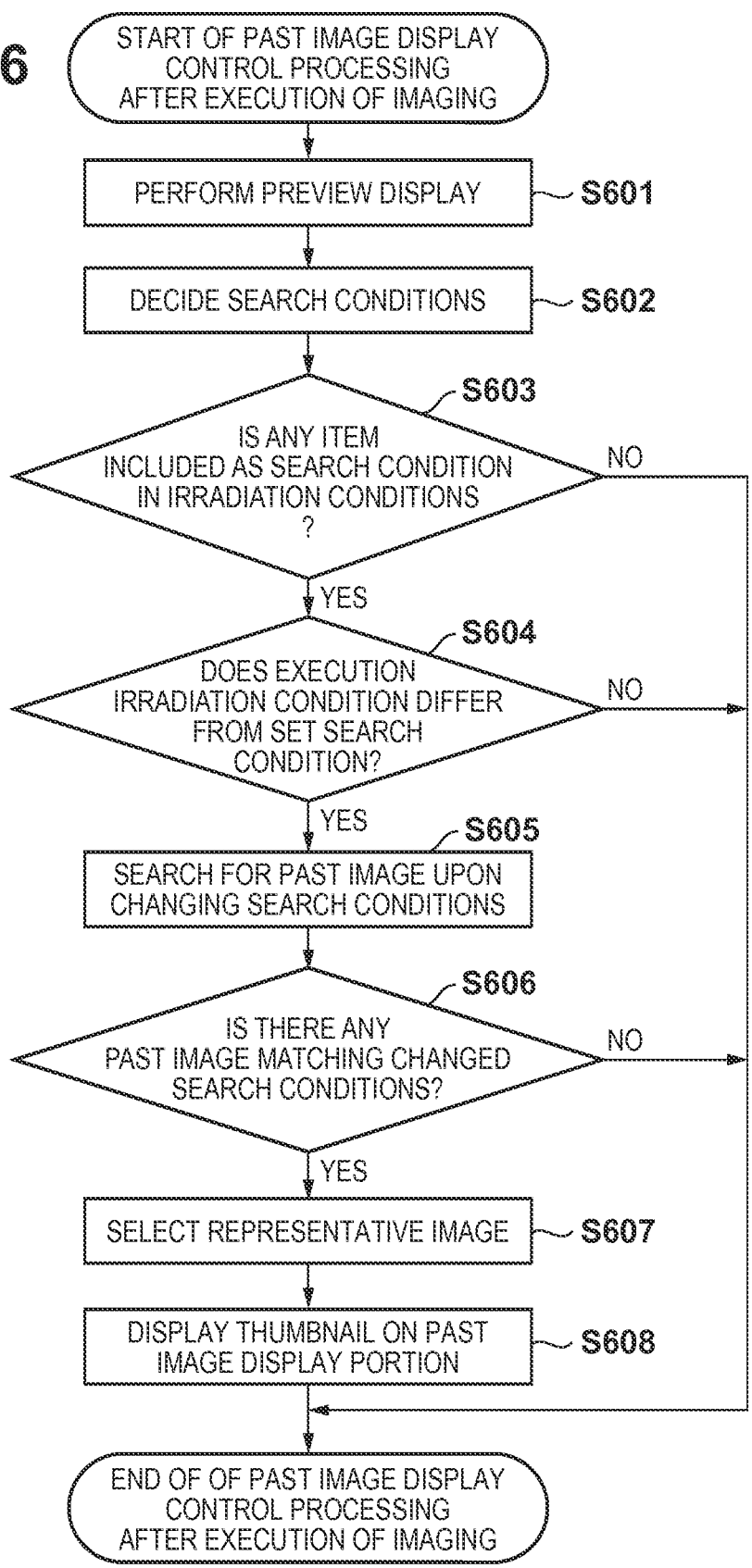
FIG. 6 is a flowchart showing a procedure for different-inspection image display control processing after the execution of imaging.

A procedure for different-inspection image display control processing after imaging in the X-ray imaging apparatus 101 will be described by using FIG. 6 with reference to FIGS. 2 and 3B. FIG. 6 is a flowchart showing a procedure for different-inspection image display control processing after the execution of imaging in the X-ray imaging apparatus 101.

When the apparatus executes imaging, the imaging execution unit 209 receives a captured image from the X-ray detector 112. Upon receiving an X-ray irradiation end notification from the X-ray generation apparatus, the imaging execution unit 209 transmits the X-ray irradiation end notification and a captured image to the inspection execution management unit 205. In addition, the imaging execution unit 209 transmits execution irradiation conditions and the X-ray irradiation end notification to the inspection execution information management unit 210. In this state, the apparatus starts different-inspection image display control processing after the execution of imaging shown in FIG. 6.

In step S601, the inspection execution management unit 205, which has received the X-ray irradiation end notification, transmits the transmitted captured image to the X-ray imaging apparatus display unit 106 via the input/output control unit 204. The X-ray imaging apparatus display unit 106 displays a thumbnail of the received captured image in the captured image thumbnail display areas 305 of the imaging technique display portion 304 (FIG. 3B). The X-ray imaging apparatus display unit 106 also preview-displays the captured image on the image display portion 302.

In step S602, the apparatus decides different-inspection image search conditions. More specifically, upon receiving the X-ray irradiation end notification from the imaging execution unit 209, the inspection execution information management unit 210 transmits a different-inspection image search condition request notification to the past inspection storage unit 211. Upon receiving the different-inspection image search condition request notification, the past inspection storage unit 211 acquires items to be used from search conditions stored in advance (the search conditions set via the display window 401). The past inspection storage unit 211 then decides specific values of the respective items of the search conditions based on patient information/inspection content identification information and imaging technique information and transmits the specific values to the inspection execution information management unit 210.

In step S603, the inspection execution information management unit 210 checks whether any irradiation condition items (the respective items on the irradiation condition information setting unit 405 in FIG. 4) are included in the transmitted search condition items. If the inspection execution information management unit 210 determines that an irradiation condition item is included in the search condition items, the process advances to step S604. If the inspection execution information management unit 210 determines that no irradiation condition is included in the search condition items, the apparatus determines that there is no need to update the representative image. The apparatus then terminates the processing.

In step S604, the apparatus checks whether there are any execution irradiation condition items ("tube voltage" and "tube current" in the case of FIG. 4) which differ in value from the irradiation condition items included in the search conditions. If the apparatus determines that there is an item which differs in value, the process advances step S605. If the apparatus determines that there is no item which differs in value, the apparatus determines that there is no need to update the representative image, and terminates the processing.

In step S605, the apparatus searches for a different-inspection image more suitable for comparison with a captured image than the currently displayed representative image. More specifically, the inspection execution information management unit 210 rewrites any items of the irradiation conditions included in the search conditions which differ in values from execution irradiation conditions with the values of the execution irradiation conditions. The inspection execution information management unit 210 further transmits the search conditions whose values have been rewritten to the past inspection storage unit 211, together with a different-inspection image search notification. Upon receiving the different-inspection image search notification, the past inspection storage unit 211 searches for past inspection information based on the search conditions whose values have been rewritten, and transmits the search result to the inspection execution information management unit 210.

In step S606, the inspection execution information management unit 210 checks whether a different-inspection image group has been transmitted as the search result. If the inspection execution information management unit 210 determines that a different-inspection image group matching the search conditions whose values have been rewritten has been transmitted, the process advances to step S607. If the inspection execution information management unit 210 determines that no different-inspection image group matching the search conditions has been transmitted, the apparatus determines that there is no need to update the representative image, and terminates the processing.

In step S607, the apparatus selects a representative image from the search result. More specifically, the inspection execution information management unit 210 selects, as a representative image, the latest different-inspection image (the different-inspection image captured at the latest imaging time) from the different-inspection image group transmitted as the search result. Note that the method of deciding representative images is not limited to this, and representative images may be decided by other methods. In addition, the number of representative images to be selected is preferably one, but may be plural depending on the size of the different-inspection image display portion 307.

In step S608, the apparatus displays a thumbnail of the representative image on the different-inspection image display portion 307, and terminates the processing. More specifically, the inspection execution management unit 205, which has received the representative image, transmits the representative image to the X-ray imaging apparatus display unit 106 via the input/output control unit 204, and causes the different-inspection image display portion 307 to display a thumbnail of the representative image. The apparatus then terminates the processing.

As described above, the X-ray imaging apparatus 101 according to this embodiment is configured to decide search conditions reflecting execution irradiation conditions at the time of imaging every time imaging operation is complete. This makes it possible to search for and display a different-inspection image corresponding to the captured image displayed on the image display portion 302. That is, it is possible to prevent the situation of displaying a different-inspection image which differs in appearance in spite of the fact that the patient and imaging portion are the same, because the irradiation conditions for the respective imaging operations differ from each other.

Although FIG. 6 has exemplified, as different-inspection image display control processing after the execution of imaging, the processing to be performed to display, on the image display portion 302, the captured image transmitted at the time of reception of an X-ray irradiation end notification, this embodiment is not limited to this. For example, similar processing is executed even in a case in which any of thumbnails displayed in the captured image thumbnail display areas 305 of the imaging technique display portion 304 is preview-selected, and a captured image corresponding to the selected thumbnail is displayed on the image display portion 302. That is, every time the captured image displayed on the image display portion 302 is switched, the apparatus executes different-inspection image display control processing after the execution of imaging shown in FIG. 6. This will switch the thumbnail of the different-inspection image displayed on the different-inspection image display portion 307 to another thumbnail suitable for comparison with the captured image displayed on the image display portion 302.

With an operation input from the X-ray imaging apparatus operation unit 105, an imaging condition or thumbnail displayed on the X-ray imaging apparatus display unit 106 is selected. This triggers the apparatus to search for a different-inspection image in accordance with the selected imaging condition or thumbnail, thereby displaying a representative different-inspection image.

Selection of one of an imaging condition and thumbnail may also select the other. The imaging condition and thumbnail may have a common selection area. The imaging condition and thumbnail may be independently selected. It is possible to select a thumbnail corresponding to a given imaging condition and display a captured image corresponding to the selected thumbnail while preparing and executing imaging by selecting another imaging condition.

Note that an operation input from the X-ray imaging apparatus operation unit 105 may perform operation other than selection of an imaging condition or thumbnail displayed on the X-ray imaging apparatus display unit 106. For example, automatic selection is possible. When the window shown in FIG. 3A is displayed, if there is only one imaging condition, the imaging condition is selected, and if there are a plurality of imaging conditions, the first one is selected. Alternatively, if imaging is executed, a thumbnail obtained by the imaging is automatically selected. Note that this embodiment is not limited to a thumbnail or imaging condition to be selected, a captured image and imaging information including the captured image may be selected.

As is obvious from the above description, the X-ray imaging apparatus 101 according to this embodiment is configured to automatically search for a different-inspection image corresponding to selected imaging technique information upon selection of the imaging technique information before imaging and display a thumbnail of the different-inspection image.

The apparatus is also configured to automatically search for a different-inspection image, every time imaging is complete and a captured image is displayed on the image display portion 302, in consideration of execution irradiation conditions at the time of imaging for the captured image. In addition, the apparatus is configured to automatically search for a different-inspection image and display a thumbnail of the image, every time a thumbnail of a captured image displayed on the imaging technique display portion 304 is preview-selected, in consideration of execution irradiation conditions at the time of imaging for the captured image corresponding to the thumbnail.

That is, the X-ray imaging apparatus 101 according to this embodiment is configured to sequentially search for a different-inspection image corresponding to imaging technique information and automatically update the different-inspection image displayed on the different-inspection image display portion 307. This makes it possible to display a different-inspection image suitable for comparison with the captured image displayed on the image display portion 302.

In addition, the X-ray imaging apparatus 101 according to this embodiment is configured to display a different-inspection image in an area (different-inspection image display portion 307) different from an area (imaging technique display portion 304) in which thumbnails of captured images are displayed. This facilitates discriminating the captured images from the different-inspection image.

Furthermore, the X-ray imaging apparatus 101 according to this embodiment is configured to display a different-inspection image upon selecting a representative image from a search result. This can prevent the different-inspection image display portion 307 which displays a different-inspection image from being wasted.

This makes it possible to improve convenience to the operator of a medical imaging apparatus capable of displaying different-inspection images.

Second Embodiment

The first embodiment is configured to automatically select a representative image from a retrieved different-inspection image group. However, this embodiment is not limited to this. For example, the embodiment may be configured to allow the operator to manually switch the automatically selected representative image to another different-inspection image of the different-inspection image group. This embodiment will be described in detail below.

<1. Description of Display Window to be Displayed when Representative Image Switching Portion is Pressed>

A display window to be used when the operator manually switches a representative image will be described first. FIG. 7 shows an example of a display window 701 to be used when switching the thumbnail of the different-inspection image displayed on a different-inspection image display portion 307 to a thumbnail of another different-inspection image. The display window 701 in FIG. 7 is displayed when the operator presses a representative image switching button 310 on a display window 301 in FIG. 3B.

As shown in FIG. 7, the display window 701 includes a patient information display portion 702, a past inspection list 703, a past inspection imaging technique list 705, and a selection end instruction portion 708.

The patient information display portion 702 is an area for displaying patient information concerning a currently executed inspection. The past inspection list 703 is an area for displaying inspection information 704 of different-inspection images acquired as a search result in the form of a list. The past inspection list 703 displays inspection content identification information such as an inspection ID and an inspection date as columns. In the case shown in FIG. 7, the past inspection list 703 is configured to display inspection information corresponding to one inspection in one row. However, inspection information corresponding to a plurality of inspections may be collectively displayed in one row depending on the situation. Alternatively, inspection information corresponding to one inspection may be separately displayed in a plurality of rows. Note that it is possible to select either a single piece of inspection information 704 or a plurality of pieces of inspection information 704 on the past inspection list 703.

The past inspection imaging technique list 705 includes an imaging technique display portion 706. The imaging technique display portion 706 includes a different-inspection image thumbnail display area 707. Imaging technique information (imaging technique name or the like) corresponding to the inspection information 704 selected by the operator from the past inspection list 703 is displayed on the imaging technique display portion 706. The apparatus displays thumbnails of all the different-inspection images captured with the inspection information 704 selected by the operator from the past inspection list 703 in the different-inspection image thumbnail display area 707.

Note that the apparatus displays, on the past inspection imaging technique list 705, information for uniquely specifying each piece of inspection information so as to facilitate discriminating each piece of past inspection information even if a plurality of pieces of past inspection information are selected on the past inspection list 703.

The selection end instruction portion 708 is a button for issuing an instruction to end selection of a representative image. Note that the display window 701 is configured to confirm the selection of a representative image by selecting an arbitrary thumbnail displayed in the different-inspection image thumbnail display area 707. However, the method of confirming the selection of a representative image is not limited to this. For example, if the operator has selected any of the thumbnails in the different-inspection image thumbnail display area 707 when pressing the selection end instruction portion 708, the different-inspection image corresponding to the selected thumbnail may be confirmed as a representative image. Note that if the operator presses the selection end instruction portion 708 while no thumbnail is selected, the apparatus does not switch the representative image.

<2. Procedure for Representative Image Switching Processing>

A procedure for representative image switching processing will be described next by using FIG. 8 with reference to FIG. 7. FIG. 8 is a flowchart showing a procedure for representative image switching processing. As shown in FIG. 8, when the operator inputs a representative image switching instruction by pressing the representative image switching button 310 on the display window 301 in step S801, the apparatus receives this instruction. More specifically, an X-ray imaging apparatus operation unit 105 transmits the representative image switching instruction to an inspection execution management unit 205 via an input/output control unit 204.

In step S802, the inspection execution management unit 205, which has received the representative image switching notification, checks whether there is any image which is currently preview-displayed. If the inspection execution management unit 205 determines that there is an image which is currently preview-displayed, the process advances to step S803. If the inspection execution management unit 205 determines that there is no image which is currently preview-displayed, the process advances to step S804.

In step S803, the apparatus acquires different-inspection image search conditions by using the imaging technique information used to capture the captured image which is currently preview-displayed. More specifically, the inspection execution management unit 205 transmits the imaging technique information used to capture the captured image which is currently preview-displayed to a past inspection management unit 208, together with a different-inspection image search condition request notification. In addition, the past inspection management unit 208 transmits patient information/inspection content identification information and the notified imaging technique information to a past inspection storage unit 211, together with the different-inspection image search condition request notification.

Upon receiving the different-inspection image search condition request notification, the past inspection storage unit 211 acquires items to be used for different-inspection image search from the stored search conditions. The past inspection storage unit 211 then decides specific values of the respective items of the search conditions based on the transmitted patient information/inspection information and imaging technique information and notifies the past inspection management unit 208 of the specific values.

In step S804, the inspection execution management unit 205 checks whether an imaging technique in a non-irradiated state is selected. If the inspection execution management unit 205 determines in step S804 that an imaging technique in a non-irradiated state is selected, the process advances to step S805. If the inspection execution management unit 205 determines in step S804 that an imaging technique in a non-irradiated state is not selected, the process advances to step S806.

In step S805, the apparatus acquires search conditions based on the imaging technique information which is currently selected for an imaging plan. Note that the contents of processing in step S805 are the same as those in step S803. In step S805, however, the inspection execution management unit 205 transmits the imaging technique information which is currently selected for an imaging plan to the past inspection management unit 208, together with a different-inspection image search request notification.

In step S806, search conditions are set by using only patient information. The contents of processing in step S806 are the same as those in step S803. In step S806, however, the inspection execution management unit 205 transmits a different-inspection image search condition request notification to the past inspection management unit 208 without adding any imaging technique information. Upon receiving the different-inspection image search condition request notification via the past inspection management unit 208, the past inspection storage unit 211 acquires only settings concerning patient information as search conditions and transmits them to the past inspection management unit 208.

Switching search conditions in accordance with an imaging state in this manner can easily switch to a desired representative image even if a desired different-inspection image is not automatically selected as a representative image.

Upon acquiring search conditions, the apparatus searches for a different-inspection image based on the decided search conditions in step S807. More specifically, the different-inspection inspection management unit 208 transmits a different-inspection image search notification to the past inspection storage unit 211, together with the search conditions. Upon receiving the different-inspection image search notification, the past inspection storage unit 211 searches for past inspection information based on the search conditions, and transmits a search result to the past inspection management unit 208.

In step S808, the apparatus displays a representative image selection window (display window 701). More specifically, the past inspection management unit 208 notifies the inspection execution management unit 205 of the search result. Upon receiving the search result, the inspection execution management unit 205 transmits a different-inspection image selection window display request notification to an X-ray imaging apparatus display unit 106 via the input/output control unit 204, together with the search result. Upon receiving the different-inspection image selection window display request notification, the X-ray imaging apparatus display unit 106 displays a different-inspection image selection window, and displays the search result on the past inspection list 703.

In step S809, the operator selects a representative image on the display window 701. When the operator selects a representative image, the X-ray imaging apparatus display unit 106 transmits information representing the selected representative image to the inspection execution management unit 205 via the input/output control unit 204. The inspection execution management unit 205 acquires the selected representative image from the past inspection storage unit 211 via the past inspection management unit 208.

In step S810, the apparatus hides the representative image selection window. More specifically, upon acquiring a representative image, the inspection execution management unit 205 transmits a representative image selection window hide request notification to the X-ray imaging apparatus display unit 106 via the input/output control unit 204. Upon receiving the representative image selection window hide request notification, the X-ray imaging apparatus display unit 106 hides the representative image selection window.

In step S811, the apparatus switches the thumbnail in a different-inspection image thumbnail display area 308 on the different-inspection image display portion 307 on a display window 301. Upon receiving a representative image, the inspection execution management unit 205 displays a thumbnail of the representative image received from the X-ray imaging apparatus display unit 106 via the input/output control unit 204 in the different-inspection image thumbnail display area 308 on the different-inspection image display portion 307.

As is obvious from the above description, the X-ray imaging apparatus 101 according to this embodiment is configured to manually change a representative image. This makes it possible to immediately switch a representative image if the displayed representative image is not a different-inspection image desired by the operator.

This can improve convenience to the operator of the X-ray imaging apparatus.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium)

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-241105, filed Oct. 31, 2012, which is hereby incorporated by reference herein in its entirety.

What is claimed is:

1. A radiation imaging control apparatus comprising:
a communication circuit for communicating with a radiation detector for obtaining a radiation image;
a processor; and
memory storing a program to be executed by the processor to:
  cause a display unit to display one or more imaging condition(s) for one inspection of an object to be imaged;
  designate one imaging condition of the one or more imaging condition(s);
  obtain, based on the designated imaging condition, a past image which is an image of the object and is of an inspection different from the one inspection;
  cause a display unit to display a past thumbnail image corresponding to the obtained past image;
  receive a captured image from the radiation detector using the communication circuit, wherein the captured image has been captured based on one of the one or more imaging condition(s); and
  cause a display unit to display the captured image, so that the at least one imaging condition, the past thumbnail image and the captured image are simultaneously displayed in one imaging window.

2. The apparatus according to claim 1, wherein, in accordance with a selection operation input of an imaging condition which has not been used for imaging among the displayed imaging conditions, the processor controls an imaging apparatus and causes a display unit to display the radiation image of the different inspection based on the imaging condition.

3. The apparatus according to claim 1, wherein, in accordance with selection of an imaging condition which has been used for imaging among the display imaging conditions, the processor causes a display unit to display a captured image obtained based on the imaging condition and displays the radiation image of the different inspection based on the imaging condition.

4. The apparatus according to claim 1, wherein
the imaging window further includes a display area for displaying the past thumbnail image of the captured image obtained based on the imaging condition, and
in accordance with selection of the past thumbnail image displayed on the imaging window, the processor causes a display unit to display a captured image obtained based on an imaging condition corresponding to the selected past thumbnail image and causes the display unit to display the radiation image of the different inspection based on the imaging condition.

5. A radiation imaging control apparatus comprising:
a communication circuit for communicating with a radiation detector for obtaining a radiation image;
a processor; and
memory storing a program to be executed by the processor to:
  obtain a first and a second imaging condition, for one inspection of an object to be imaged;
  receive a first captured image from the radiation detector using the communication circuit, wherein the first captured image has been captured based on a first imaging condition;
  cause a display unit to display a first thumbnail image corresponding to the first captured image;
  designate the first thumbnail image;
  obtain, based on first imaging condition corresponding to the designated first thumbnail image, a past image which is an image of the object and is of an inspection different from the one inspection;
  cause a display unit to display a past thumbnail image corresponding to the obtained past image;
  receive a second captured image from the radiation detector using the communication circuit, wherein the captured image has been captured based on the second imaging condition; and
  cause a display unit to display the second captured image, so that the first thumbnail image, the past thumbnail image and the second captured image are simultaneously displayed in one imaging window.

6. A method of controlling a radiation imaging control apparatus which has a communication circuit for communicating with a radiation detector for obtaining a radiation image, a processor and memory storing a program to be executed by the processor, the method comprising:
causing a display unit configured to display one or more imaging condition(s) for one inspection of an object to be imaged;
designating one imaging condition of the one or more imaging condition(s);
obtaining, based on the designated imaging condition, a past image which is an image of the object and is of an inspection different from the one inspection;
causing a display unit to display a past thumbnail image corresponding to the obtained past image;
receiving a captured image from the radiation detector using the communication circuit, wherein the captured image has been captured based on one of the one or more imaging condition(s); and
causing a display unit to display the captured image, so that the one or more imaging condition(s), the past thumbnail image and the captured image are simultaneously displayed in one imaging window.

7. A method of controlling a radiation imaging control apparatus which has a communication circuit for communicating with a radiation detector for obtaining a radiation image, a processor and memory storing a program to be executed by the processor, the method comprising:
obtaining a first and a second imaging condition, for one inspection of an object to be imaged;
receiving a first captured image from the radiation detector using the communication circuit, wherein the first captured image has been captured based on a first imaging condition;
causing a display unit to display a first thumbnail image corresponding to the first captured image;
designating the first thumbnail image;
obtaining, based on first imaging condition corresponding to the designated first thumbnail image, a past image which is an image of the object and is of an inspection different from the one inspection;
causing a display unit to display a past thumbnail image corresponding to the obtained past image;
receiving a second captured image from the radiation detector using the communication circuit, wherein the captured image has been captured based on the second imaging condition; and
causing a display unit to display the second captured image, so that the first thumbnail image, the past thumbnail image and the second captured image are simultaneously displayed in one imaging window.

8. A non-transitory computer readable storage medium storing a program for causing a computer to execute a method of controlling a radiation imaging control apparatus which has a communication circuit for communicating with a radiation detector for obtaining a radiation image, a processor and memory storing the program, to be executed by the processor, the method comprising:
causing a display unit configured to display one or more imaging condition(s) for one inspection of an object to be imaged;
designating one imaging condition of the one or more imaging condition(s);
obtaining, based on the designated imaging condition, a past image which is an image of the object and is of an inspection different from the one inspection;
causing a display unit to display a past thumbnail image corresponding to the obtained past image;
receiving a captured image from the radiation detector using the communication circuit, wherein the captured image has been captured based on one of the one or more imaging condition(s); and
causing a display unit to display the captured image, so that the one or more imaging condition(s), the past thumbnail image and the captured image are simultaneously displayed in one imaging window.

9. A non-transitory computer readable storage medium storing a program for causing a computer to execute a method of controlling a radiation imaging control apparatus which has a communication circuit for communicating with a radiation detector for obtaining a radiation image, a processor and memory storing the program to be executed by the processor, the method comprising:
obtaining a first and a second imaging condition, for one inspection of an object to be imaged;
receiving a first captured image from the radiation detector using the communication circuit, wherein the first captured image has been captured based on a first imaging condition;
causing a display unit to display a first thumbnail image corresponding to the first captured image;
designating the first thumbnail image;
obtaining, based on first imaging condition corresponding to the designated first thumbnail image, a past image which is an image of the object and is of an inspection different from the one inspection;
causing a display unit to display a past thumbnail image corresponding to the obtained past image;
receiving a second captured image from the radiation detector using the communication circuit, wherein the captured image has been captured based on the second imaging condition; and
causing a display unit to display the second captured image, so that the first thumbnail image, the past thumbnail image and the second captured image are simultaneously displayed in one imaging window.

10. A medical imaging apparatus which captures a medical image based on imaging technique information, the apparatus comprising:
an obtaining unit configured to obtain items of imaging technique information of a first inspection of an object;
a storage unit configured to store past medical images of a second inspection of the object;
a search unit configured to search, based on one item of the items of the imaging technique information, the storage unit to obtain a past medical image of the stored past medical images; and
a display control unit configured to display first thumbnails of first medical images captured based on the items of imaging technique information in a first area on a display window, display a past thumbnail of the obtained past medical image in a second area, and display, in a third area, one of the first medical images corresponding to a selected first thumbnail of the first thumbnails displayed in the first area,
wherein the search unit is configured to specify an item of the items of the imaging technique information based on the selected first thumbnail, for obtaining the past medical image, and
the display control unit updates, in a case in which another first thumbnail of the first thumbnails displayed in the first area is selected, display in the second area by using another past thumbnail of another past image, of the stored past images, obtained by the search unit.

11. The apparatus according to claim 10, wherein the display in the third area is changed every time a medical image is captured.

12. The apparatus according to claim 10, wherein the display in the third area is changed every time selection of a thumbnail displayed in the first area is switched.

13. The apparatus according to claim 10, wherein when imaging technique information is selected upon capturing the medical image, the search unit further searches for a different-inspection image stored in the storage unit based on the selected imaging technique information.

14. The apparatus according to claim 10, wherein the display control unit selects a first different-inspection image as a representative image from different-inspection images retrieved based on the imaging technique information, and displays a thumbnail of the selected representative image in the second area.

15. The apparatus according to claim 14, wherein the display control unit selects, as the representative image, a different-inspection image, of the different-inspection images retrieved based on the imaging technique information, which is captured at a latest imaging time.

16. The apparatus according to claim 14, further comprising a switching unit configured to switch the representative image selected by the display control unit to another different-inspection image.

17. The apparatus according to claim 10, further comprising a search condition setting unit configured to set an item, of the imaging technique information, which is used for a search by the search unit.

18. The apparatus according to claim 17, wherein the item used for the search includes at least one of an imaging technique name, an imaging portion, an imaging direction, an irradiation condition, and an image processing parameter.

19. A medical image display method for a medical imaging apparatus which captures a medical image based on imaging technique information, the method comprising:
   an obtaining step of obtaining items of imaging technique information of a first inspection of an object;
   a storage step of storing past medical images of a second inspection of the object;
   a search step of searching, based on one item of the items of the imaging technique information, the storage unit to obtain a past medical image of the stored past medical images;
   a first display control step of displaying first thumbnails of first medical images captured based on the items of imaging technique information in a first area on a display window;
   a second display control step of displaying a past thumbnail of the obtained past medical image in a second area; and
   a third display control step of displaying, in a third area, one of the first medical images corresponding to a selected first thumbnail of the first thumbnails displayed in the first area,
   wherein, in the search step, an item of the items of the imaging technique information is specified based on the selected first thumbnail for obtaining the past medical image, and
   in the second display control step, in a case in which another first thumbnail of the first thumbnails displayed in the first area is selected, display in the second area is updated by using another past thumbnail of another past image, of the stored past images, obtained by the search unit.

20. A non-transitory computer readable storage medium storing a program for causing a computer to function as each unit of a medical imaging apparatus which captures a medical image based on imaging technique information, the medical imaging apparatus comprising:
   an obtaining unit configured to obtain items of imaging technique information of a first inspection of an object;
   a storage unit configured to store past medical images of a second inspection of the object;
   a search unit configured to search, based on one item of the items of the imaging technique information, the storage unit to obtain a past medical image of the stored past medical images; and
   a display control unit configured to display first thumbnails of first medical images captured based on the items of imaging technique information in a first area on a display window, display a past thumbnail of the obtained past medical image in a second area, and display, in a third area, one of the first medical images corresponding to a selected first thumbnail of the first thumbnails displayed in the first area,
   wherein the search unit is configured to specify an item of the items of the imaging technique information based on the selected first thumbnail for obtaining the past medical image, and
   the display control unit updates, in a case that another first thumbnail of the first thumbnails displayed in the first area is selected, display in the second area by using another past thumbnail of another past image, of the stored past images, obtained by the search unit.

21. A radiation imaging control apparatus comprising:
   a communication circuit configured to communicate with a radiation detector for obtaining a radiation image;
   a display control unit configured to display one or more imaging condition(s) for one inspection of an object to be imaged;
   a designation unit configured to designate one imaging condition of the one or more imaging condition(s);
   an obtaining unit configured to obtain, based on the designated imaging condition, a past image which is an image of the object and is of an inspection different from the one inspection; and
   a receiving unit configured to receive a captured image from the radiation detector using the communication circuit, wherein the captured image has been captured based on one of the one or more imaging condition(s),
   wherein the display control unit causes a display unit to display a past thumbnail image corresponding to the obtained past image, and
   the display control unit causes a display unit to display the captured image, so that the one or more imaging condition(s), the past thumbnail image and the captured image are simultaneously displayed in one imaging window.

* * * * *